United States Patent [19]

Press et al.

[11] Patent Number: 4,775,694

[45] Date of Patent: Oct. 4, 1988

[54] ANTITUSSIVE COMPOSITION

[75] Inventors: Eugene G. Press, Elizabeth; Thomas M. Tencza, Wallington; F. Henry Merkle, Scotch Plains, all of N.J.

[73] Assignee: Bristol-Myers Company, New York, N.Y.

[21] Appl. No.: 31,143

[22] Filed: Mar. 24, 1987

Related U.S. Application Data

[63] Continuation of Ser. No. 783,284, Sep. 30, 1985, abandoned.

[51] Int. Cl.$^4$ .............................................. A61K 31/24
[52] U.S. Cl. .................................. 514/535; 514/850; 514/938
[58] Field of Search ................ 514/535, 536, 850, 938

[56] References Cited

U.S. PATENT DOCUMENTS 2,714,608 8/1955 Matter ..................................... 560/5

OTHER PUBLICATIONS

Physicians Desk Reference (PDR), 26th ed, 1972, p. 664.
Lachman et al.—"The Theory & Practice of Industrial Pharmacy", 2nd ed. 1976, 184–186 & 196–200.

*Primary Examiner*—Leonard Schenkman
*Attorney, Agent, or Firm*—Morton S. Simon; Sandra M. Person

[57] ABSTRACT

The invention relates to an oral pharmaceutical composition containing benzonatate. More particularly it concerns a composition of this character having improved taste and demulcency characteristics as well as one which minimizes the local anaesthesia to the oral mucosa brought about by the benzonatate.

10 Claims, No Drawings

ANTITUSSIVE COMPOSITION

This is a continuing application of Ser. No. 783,284 filed Sept. 30, 1985, now abandoned.

Benzonatate is a well-known pharmaceutically active antitussive compound known chemically as nonaethyleneglycol monomethyl ether of p-n-butylaminobenzoate which as the formula

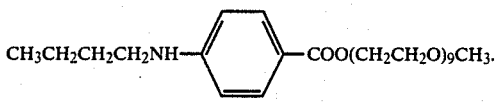

Although this material is an effective antitussive agent it has one particularly distressing drawback which is that when taken orally it produces severe local anaesthesia of the oral mucosa.

The seriousness of this problem is reflected in the Food and Drug Administration's regulations regarding the marketing of products containing benzonatate. Benzonatate was listed by the Food and Drug Administration as a Category I antitussive with the provision that the drug should be marketed in a dosage form that does not release the drug into the oral cavity because of its severe anaesthetic effect. It was stated that in adverse reaction reports, an anaphylactoid reaction resulted in one individual as a result of the drug dissolving in the mouth. Because of this effect, the drug has been sold alone or in combination only in perle or soft gelatin capsules designed to be swallowed whole. These products bear cautionary statements such as "If perles are chewed or dissolved in the mouth, oropharyngeal anaesthesia will develop rapidly. CNS stimulation may cause restlessness and tremors which may proceed to clonic convulsions followed by profound CNS depression".

It has now been found that the above disadvantages may be avoided if substantially all of the benzonatate is incorporated in the oil phase of an oil-in-water-emulsion.

The benzonatate has preferential solubility in this oil and the emulsion vehicle effectively "tames" the benzonatate so that the anaesthetic effect is not more severe than one experiences with e.g. benzocaine.

Suitably the oil of the oil-in-water emulsions useful in accordance with this invention is a caprylic/capric triglyceride, i,e, a mixed triester of glycerin and caprylic and capric acids. Materials of this type are commercially available from a number of manufacturers. One such material is sold by Stokely Van-Camp under the trade name Captex 300.

Other edible oils can also be used, either synthetic or natural, that are compatible with the benzonatate. Such other varieties of oils include olive oil, corn oil, cottonseed oil, peanut oil, sesame oil, safflower oil, sunflower oil, mineral oil and the like. Generally the quantity of oil in the oil-in-water emulsion will constitute between about 2% to about 50% by weight based on the total weight of the composition, with the preferred range being from about 8% to about 14% on the same weight basis.

All that is essential with respect to the concentration of benzonatate that an effective antitussive dose should be administered with a convenient volume of liquid, such as from 1 to 2 tablespoons. Usually, the benzonatate will be present in the composition at a level of from about 0.30% to about 1.00% by weight based on the total weight of the composition. Optimally, this concentration will be from about 0.32% to about 0.64% on the same weight basis.

In preparing the compositions of this invention an emulsifying agent is suitably employed which is capable of forming an oil-in-water emulsion with the ingredients so that the benzonatate is essentially all contained in the oil phase. A number of emulsifying agents are known in the prior art which are of this character. By way of example such agents as long chain fatty acid esters of glycerin polymers (e.g. Santone 8-1-0, a polyclyceryl-8 oleate); polysorbates; poloxamers; anionic surfactants; and polyglycol fatty acid esters can be used. The emulsifying agents of choice are the long chain fatty acid esters of glycerin polymers and particularly polyglyceryl-8 oleate. The emulsifying agents can be present in the composition at a level to insure the formation of the oil-in-water emulsion. This ordinarily amounts to from about 0.12% to about 3.12% by weight based on the total weight of the composition with the preferred range being from about 0.50% to about 0.9% on the same weight basis.

The water phase of the oil-in-water emulsion composition of this invention is usually the major component of the composition. It comprises the continuous phase of the emulsion and may have dissolved in it one or more of the ingredients of the composition. As a general rule the water constitutes from about 40% to about 95% by weight based on the total weight of the composition. Preferably water comprises from about 45% to about 70% this composition on the same weight basis.

Suspension stabilizing agents can also be suitably employed. Gums, such as xanthan gum, and also materials such a carbomers, acacia, agar, sodium alginate, bentonite, carboxymethylcellulose sodium, carrageenan, gelatin, hydroxyethylcellulose, hydroxypropylcellulose, hydroxypropylmethylcellulose, methylcellulose, povidone, tragacanth and magnesium aluminum silicate, and the like materials known for this purpose, can be suitably employed.

In addition to the foregoing ingredients the compositions of interest can also contain other ingredients, such as preservatives (e.g. ethanol), flavoring agents (e.g. sugar, cream flavorings), chelating agents, texture enhancing ingredients (e.g. sodium caseinate), and the like.

The composition of the present invention can be suitably prepared by the following procedure. Xanthan gum is prepared as a 2% suspension in water by adding the powder slowly to water with mixing then warming to 70° C. for about five minutes, followed by forced cooling to 40° C. Sucrose is separately dissolved to obtain a 65% by weight solution in water, by warming to 65° C. followed by cooling to 40° C. The two parts so prepared are mixed while the required amounts of water and alcohol are added, with some of the required amount of water being set aside for later addition. Captex 300, Santone 8-1-0, and benzonatate are mixed and warmed to 60° C. This mixture is slowly added to batch while homogenizing. Disodium edetate is prepared as a 10% solution in water and then is added, followed by addition of flavoring. Sodium caseinate is prepared separately as a 15% suspension in water by mixing and heating to 90° C. until it is smooth and uniform. Then it is cooled to 40° C. and is added to the batch.

The following examples are given further to illustrate the present invention. It is to be understood, however, that the invention is not limited thereto.

| Benzonatate cream cough syrup formulations | | | | |
|---|---|---|---|---|
| | EXAMPLE 1 BD-3198-71A | | EXAMPLE 2 BD-3198-74A | |
| | % w/w | mg/30 ml | % w/w | mg/15 ml |
| 1. Xanthan Gum (Keltrol) | 0.300 | 94.500 | 0.300 | 47.25 |
| 2. Ethyl Alcohol 95% USP | 11.800* | 3717.000 | 11.800* | 1858.50 |
| 3. Sucrose, Fine Gran. | 20.760 | 6539.400 | 20.760 | 3269.70 |
| 4. Captex 300 ($C_6/C_{10}$ triglyceride) | 8.000 | 2520.000 | 8.000 | 1260.00 |
| 5. Santone 8-1-0 | 0.500 | 157.500 | 0.500 | 78.75 |
| 6. Benzonatate N.F. | 0.317 | 99.855 | 0.634 | 99.85 |
| 7. Disodium Edetate, Dihydrate | 0.004 | 1.260 | 0.004 | 0.63 |
| 8. Cream flavor | 0.300 | 94.500 | 0.300 | 47.25 |
| 9. Sodium Caseinate (Amer. Caseine Co.) | 2.500 | 787.500 | 2.505 | 393.75 |
| 10. Dist. Water Q.S. to | 100.000 | 31500.000 | 100.000 | 15750.00 |

*Equivalent to 15% by volume.

The specific gravity of the resulting material is 1.05 and the pH is 7.0.

We claim:

1. An orally administerable oil-in-water emulsion composition having a continuous water phase and a discontinuous oil phase, containing an antitussively effective amount of benzonatate essentially all of which is contained in the discontinuous oil phase of the emulsion, whereby upon oral ingestion the contact of the benzonatate with the oral mucosa, and any anaesthestic effect from such contact, are minimized.

2. The emulsion composition of claim 1 wherein said antitussively effective amount is from about 0.30% to about 1% by weight, based on the total weight of said composition, and the oil constitutes between about 2% to about 50% by weight, based on the total weight of the composition.

3. The emulsion composition of claim 1, wherein said antitussively effective amount is from about 0.32% to about 0.64% by weight, based on the total weight of said composition, and the oil constitutes between about 8% to about 14% by weight based on the total weight of the composition.

4. The emulsion composition of claims 1, 2, or 3, further containing an emulsifier.

5. The emulsion composition of claims 4, wherein the emulsifier is a long chain fatty acid ester of a glycerin polymer.

6. The emulsion composition of claim 5 wherein said ester is polyglyceryl-8 oleate.

7. The emulsion composition of claim 5 wherein the oil phase of said oil-in-water emulsion comprises a mixed triester of glycerin and caprylic and capric acids.

8. The emulsion composition of claims 4, wherein said emulsifier is present in said composition at a level in the range of from about 0.50% to about 0.90% by weight, based on the total weight of the composition.

9. The emulsion composition of claim 1, 2 or 3 wherein the oil phase of said oil-in-water emulsion comprises a mixed triester of glycerin and caprylic and capric acids.

10. A process for relieving coughing in a human, which comprises administering to said human the composition of claims 1, 2 or 3.

* * * * *